US006921391B1

United States Patent
Barker et al.

(10) Patent No.: US 6,921,391 B1
(45) Date of Patent: Jul. 26, 2005

(54) FLUID INFUSION DEVICE WITH RETRACTABLE NEEDLE

(75) Inventors: John Barker, Ventura, CA (US);
Michael J. Botich, Reno, NV (US);
Thor R. Halseth, Simi Valley, CA (US)

(73) Assignee: MDC Investment Holdings, Inc., Wilmington, DE (US)

( * ) Notice: Subject to any disclaimer, the term of this patent is extended or adjusted under 35 U.S.C. 154(b) by 0 days.

(21) Appl. No.: 09/786,398

(22) PCT Filed: Aug. 28, 1999

(86) PCT No.: PCT/US99/19763

§ 371 (c)(1),
(2), (4) Date: Sep. 20, 2001

(87) PCT Pub. No.: WO00/12160

PCT Pub. Date: Mar. 9, 2000

Related U.S. Application Data

(63) Continuation of application No. PCT/US99/19763, filed on Aug. 28, 1999, now Pat. No. 6,009,828.

(51) Int. Cl.[7] .............................................. A61M 25/00
(52) U.S. Cl. ....................................... 604/284; 604/905
(58) Field of Search .......................... 604/164.12, 198, 604/171, 110, 500, 506, 507, 508, 513, 82, 86, 88, 284, 411, 905

(56) References Cited

U.S. PATENT DOCUMENTS

| | | | | |
|---|---|---|---|---|
| 4,311,137 A | * | 1/1982 | Gerard | ......................... 604/28 |
| 5,129,884 A | * | 7/1992 | Dysarz | ................... 604/164.08 |
| 5,195,980 A | * | 3/1993 | Catlin | ......................... 604/167 |
| 5,261,889 A | * | 11/1993 | Laine et al. | ........... 604/164.11 |
| 5,338,314 A | | 8/1994 | Ryan | |
| 5,403,284 A | * | 4/1995 | Gross | .................... 604/167.03 |
| 5,632,735 A | | 5/1997 | Wyatt | |
| 5,755,709 A | * | 5/1998 | Cuppy | .................... 604/164.12 |
| 6,371,944 B1 | * | 4/2002 | Liu et al. | ..................... 604/284 |
| 6,398,743 B1 | * | 6/2002 | Halseth et al. | .............. 600/585 |

* cited by examiner

Primary Examiner—Manuel Mendez
(74) Attorney, Agent, or Firm—Stephen H. Eland; Dann, Dorfman, Herrell and Skillman

(57) ABSTRACT

An infusion device is provided for use with an intravenous catheter connected to a primary fluid supply. A Y site (92) is in fluid communication with the catheter (90). The infusion device is releasably connectable with the Y site (92) to connect a secondary fluid supply (97) to the catheter (40). The infusion device includes a retractable needle (70) that is retractable after use.

16 Claims, 4 Drawing Sheets

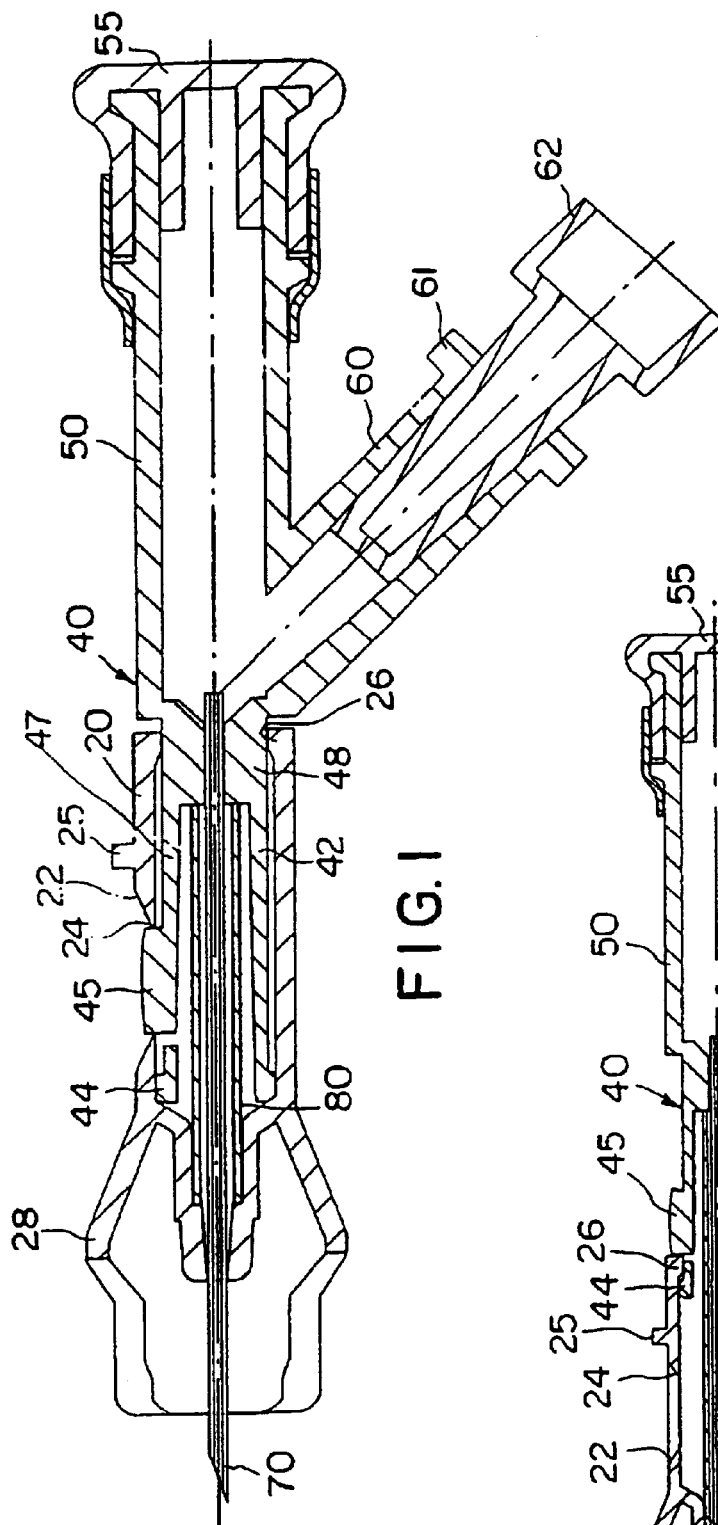

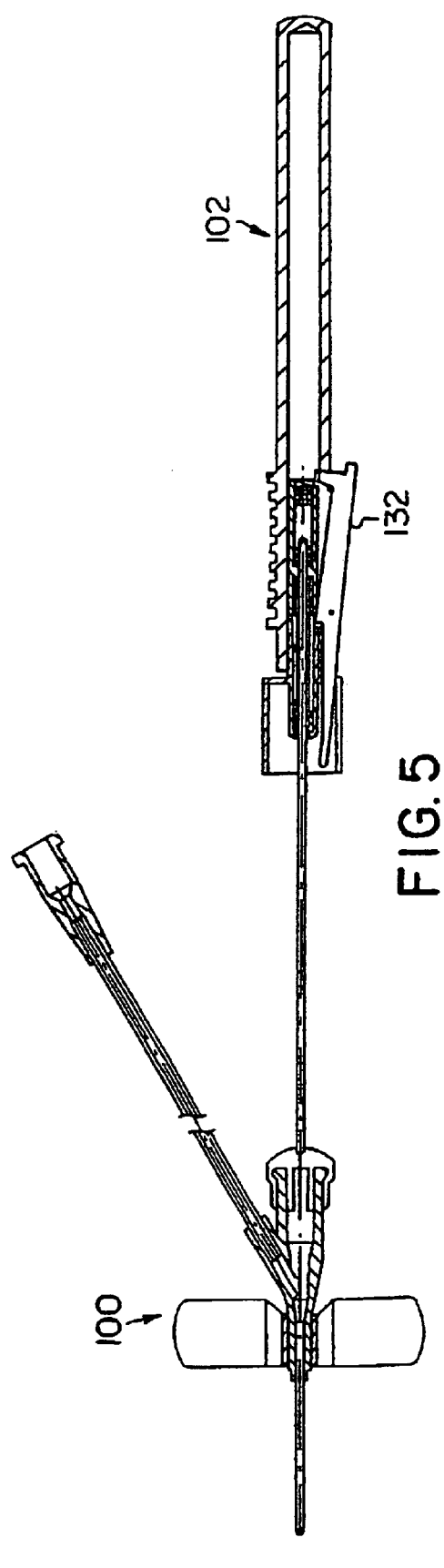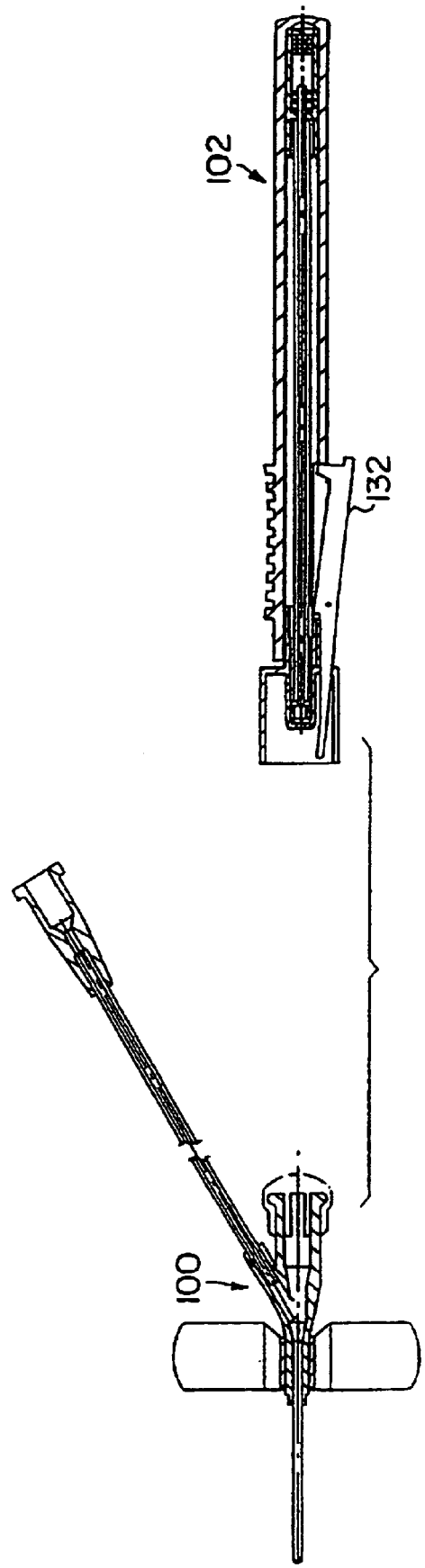

FLUID INFUSION DEVICE WITH RETRACTABLE NEEDLE

CROSS REFERENCE TO RELATED APPLICATION

Priority is claimed herein to U.S. Appl. No. 60/098,280, filed Aug. 28, 1998, which is incorporated by reference herein.

FIELD OF THE INVENTION

The present invention relates to an apparatus for the transmission of fluids. In particular, the invention relates to a retractable needle apparatus for penetrating the seal of an intravenous port and for providing a flow of fluid to or from the port.

BACKGROUND OF THE INVENTION

Intravenous therapy is widely used in medical practice to administer hydration fluids, nutritional fluids, medical fluids, or blood products directly to the circulatory system of a patient. Various types of catheters, such as peripheral catheters, central catheters or surgically implanted catheters, may be inserted into a patient to provide a route for administration of such fluids. During intravenous therapy, it is often desirable to connect to the catheter an intravenous fluid supply system that includes one or more injection ports for intermittent or continuous supply of desired fluids or combination of fluids to the patient.

A peripheral catheter, for example, may be connected by intravenous tubing with a supply of a hydrating solution, such as a saline solution, to provide a flow of such fluid to the patient. In order to provide for supplementing or replacing the flow of saline solution with another fluid, a so-called "Y-site" having a releasable injection port may be connected along the intravenous tubing. When administration of a second fluid is desired, the injection port may be punctured by a hollow needle that is connected with an external supply of the second fluid. After the desired quantity of second fluid has been administered, the needle is then removed from the injection port. The intravenous therapist must then safely discard the contaminated needle associated with the exhausted supply of fluid. Due to concerns about the handling and disposal of medical devices having contaminated needles, it is desirable to provide a device that can be utilized to infuse a secondary supply of medicinal fluid, and can be rendered safe after use.

DESCRIPTION OF THE DRAWINGS

All of the objects of the present invention are more fully set forth hereinafter with reference to the accompanying drawings, wherein:

FIG. 1 is a cross-sectional view of a retractable needle apparatus according to the present invention;

FIG. 2 is a cross-sectional view of the device illustrated in FIG. 1, illustrating the needle in a retracted position;

FIG. 5 is a sectional view of the catheter and insertion device of FIG. 4 shown in a second configuration where the insertion device is being withdrawn from the catheter; and FIG. 6 is a sectional view of the catheter and insertion device of FIG. 4 shown in a final de-coupled configuration of FIG. 1.

DETAILED DESCRIPTION OF THE PREFERRED EMBODIMENTS

Figure 3:
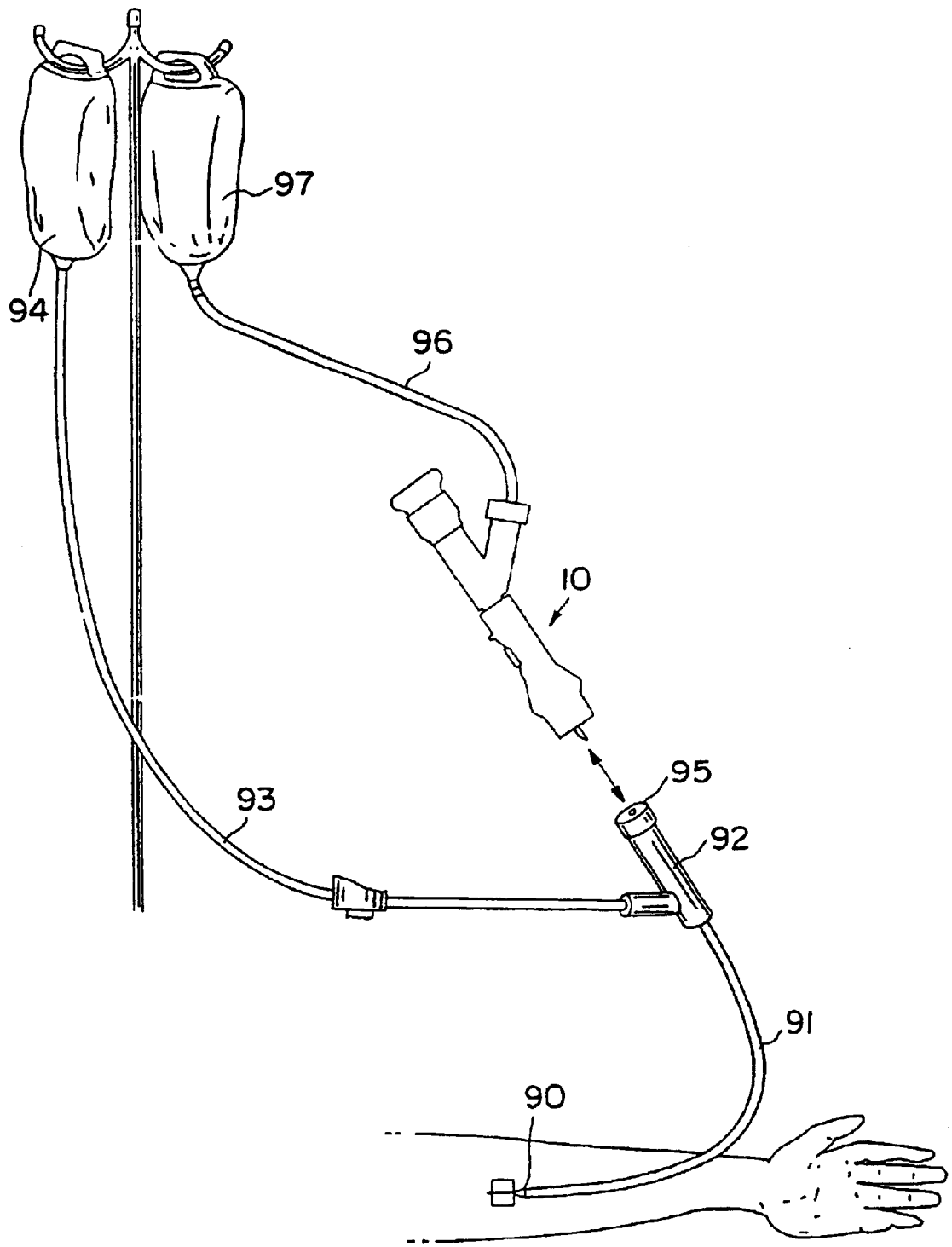
FIG. 3 is a diagramic view illustrating use of the apparatus

Referring now to the drawings in general and to FIG. 3 specifically, an infusion device 10 is illustrated in connection with an intravenous supply for supplying medicinal fluid to a patient. A catheter 90 is inserted intravenously into a patient. A fluid line connects the catheter 90 with a Y-site 92. The Y-site 92 in turn is connected to a primary line 93 that feeds fluid from a primary reservoir 94 to the catheter 90. In addition, the Y-site 92 has a port for connecting a secondary supply line. The port is covered by a piercable septum 95. The infusion device 10 has a needle 70 for piercing the septum 95 of the Y-site. The infusion device 10 is connected to a secondary supply line 96, which is in turn connected to a secondary reservoir 97 containing medicinal fluid. In this way, medicinal fluid can be fed to the catheter from both the primary reservoir 94 and the secondary reservoir 97. After use, the infusion device 10 can be removed from the Y-site and the sharpened end of the needle 70 can be retracted into the device to prevent inadvertent contact with the used needle.

The infusion device 10 includes a housing 20 and a Y-port 40 slidably displaceable within the housing. A needle 70 attached to the Y-port 40 projects forwardly from the forward end of the housing 20. A spring 80 biases the needle 70 rearwardly into a retracted position within the housing 20. An actuator button 45 is connected to the Y-port 40. The button 45 engages an aperture 22 in the housing 20 to retain the needle 70 in the extended position projecting forwardly from the housing 20. The needle 70 is retracted into the housing by depressing the button 45.

The housing 20 includes a generally cylindrical barrel having an open rearward end and a generally closed forward end. The forward end of the housing tapers inwardly forming a reduced diameter tip having an opening for receiving the needle 70. The aperture 22 formed in the side of the housing 20 engages the button 45 as is discussed further below.

Additionally, a generally bell-shaped connector 28 flares radially outwardly from the forward end of the housing 20, circumscribing the nose of the housing. The connector 28 is removably connectable with the Y-site 92. To connect the device 10 to the Y-site 92, the connector 28 snaps over the septum 95 forming a snap-fit with the Y-site.

The Y-port 40 is slidably displaceable within the housing 20. The Y-port includes a generally cylindrical hollow body 42 disposed within the housing 20. A central conduit 50 extends rearwardly from the body 42 substantially parallel to the longitudinal axis of the body. A Y-tube 60 extends transverse the central conduit 50 intersecting the central conduit so that the Y-tube and the central conduit are in fluid communication.

The rearward end of the central conduit 50 is generally opened. A piercable septum 55 encloses the open end of the central conduit 50 forming a fluid-tight seal. In addition, the rearward end of the central conduit is configured to cooperate with the connector 28 of the housing so that a second infusion device can be connected to the end of the central conduit. In this way, a plurality of infusion devices 10 can be interconnected so that fluid from a plurality of fluid supplies can be fed to the catheter. Specifically, the rearward end of the central conduit is configured so that a circumferential flange flares radially outwardly from the rearward end of the central conduit 50. In this way, the rearward end of the central conduit forms a releasable snap-fit with the connector 28 of a similar infusion device.

The Y-tube 60 provides a connector for connecting the secondary supply line 96 to the Y-tube. In the present instance, male threaded portion 61 is formed on the exterior of the Y-tube. The threaded portion 61 is cooperable with a typical lever-hub for connecting the secondary supply line 96 to the Y-tube. Alternatively, the secondary supply line can be integrally formed or fixedly connected with the Y-tube 60. Prior to use, a removable plug 62 plugs the Y-tube to prevent contamination.

The rearward end of the Y-port body 42 projects inwardly, forming a constricted neck 48 having a reduced diameter bore for receiving the needle 70. The rearward end of the needle 70 extends through the constricted neck 48 and is fixedly connected to the body 42 so that the rearward end of the needle projects rearwardly from the constricted neck 48. Preferably, the needle 70 is attached to the body 42 by epoxy. In this way, the needle is fixedly connected to the Y-port so that the needle is in fluid communication with the central conduit 50 and the Y-tube 60. A compression spring 80 is disposed around the needle 70 and bears against the Y-port body 42, fin biasing the Y-port body and the attached needle rearwardly.

The actuator button 45 releasably retains the Y-port body 42 against the bias of the spring 80. The actuator button 45 is attached to the Y-port body 42 by a radially deformable resilient arm 47. The arm 47 biases the button 45 radially outwardly so that the button 45 projects through the aperture 22 in the side of the housing 20. The rearward edge of the button 45 forms a shoulder that engages the rim 24 of the aperture 22. In this way, the button 45 impedes rearward displacement of the Y-port 40. Retraction of the needle is effectuated by depressing the button 45 so that the rear shoulder of the button 45 is displaced radially inwardly beyond the rim 24 of the aperture 22. The spring 80 then propels the Y-port 40 and the attached needle 70 rearwardly so that the sharpened end of the needle is safely withdrawn within the housing 20. Preferably, the device includes an element for preventing premature actuation of retraction. In the present instance, a tab projects upwardly from the housing 20 providing a fence to prevent the operator from inadvertently actuating the button to retract the needle prematurely.

A circumferential flange 44 on the exterior on the forward end of the Y-port body 42 operates to limit the rearward displacement of the Y-port body 42. As shown in FIG. 2, when the needle is retracted, the circumferential flange 44 on the Y-port body 42 engages an annular flange 26 that projects inwardly from the rearward edge of the housing 20. In this way, the engagement between the circumferential flange 44 and the annular flange 26 operates as a stop limiting continued rearward displacement of the Y-port body relative to the housing 20.

The needle 70 is maintained in the retracted position by the engagement of the button 45 with the interior annular flange 26 in the housing 20. The forward end of the button 45 forms a shoulder that abuts the rearward surface of the annular flange 26. During retraction, the flexible arm 47 is displaced radially inwardly so that the button passes through the reduced diameter formed by the annular flange 26. After the button is displaced rearwardly of the annular flange 26, the resilient arm 47 flexes radially outwardly. If the Y-port hub 42 is then urged forwardly to re-extend the needle 70, the forward edge of the button 45 engages the outer surface of the annular flange 26 to prevent reinsertion of the Y-port 40 into the housing 20. Accordingly, the engagement between the button 45 and the annular flange 26 prevents reextension of the needle after retraction.

In light of the foregoing, the infusion device 10 operates as follows. The catheter 90 is inserted intravenously into a patient. The catheter 90 is connected to the primary line 93 for supplying medicinal fluid from the primary reservoir 94. The Y-site 92 is in fluid communication with the catheter 90 and the primary reservoir 94. The needle 70 of the infusion device pierces the Y-site septum 95 and the infusion device is connected to the Y-site. The Y-site septum 95 frictionally engages the needle 40 and forms a fluid light seal around the needle. The infusion device 10 is connected to a secondary fluid reservoir 97. If desired, a second infusion device can be attached to the first infusion device to provide fluid from a tertiary fluid supply. In the same way, a series of infusion devices can be serially connected to the Y-site 92 to provide fluid from a plurality of fluid supplies.

After use the infusion device is disconnected from the Y-site 92 and the needle 70 is retracted by depressing the actuator button 45. Preferably, the spring 80 is selected so that prior to retraction the frictional force between the Y-site septum 95 and the needle 70 is greater than the rearward biasing force of the spring 80. In this way, depressing the button 45 before withdrawing the needle 70 from the Y-site septum 95 will not effectuate retraction. Accordingly, preferably, after use the operator continually depresses the button 45 while withdrawing the needle 70 from the Y-site septum 95. Therefore, as soon as the needle is withdrawn from the septum the needle will be retracted so that the needle is not exposed after being withdrawn from the Y-site. Alternatively, the operator can depress the button after withdrawing the device from the septum to effectuate retraction.

Figure 4:
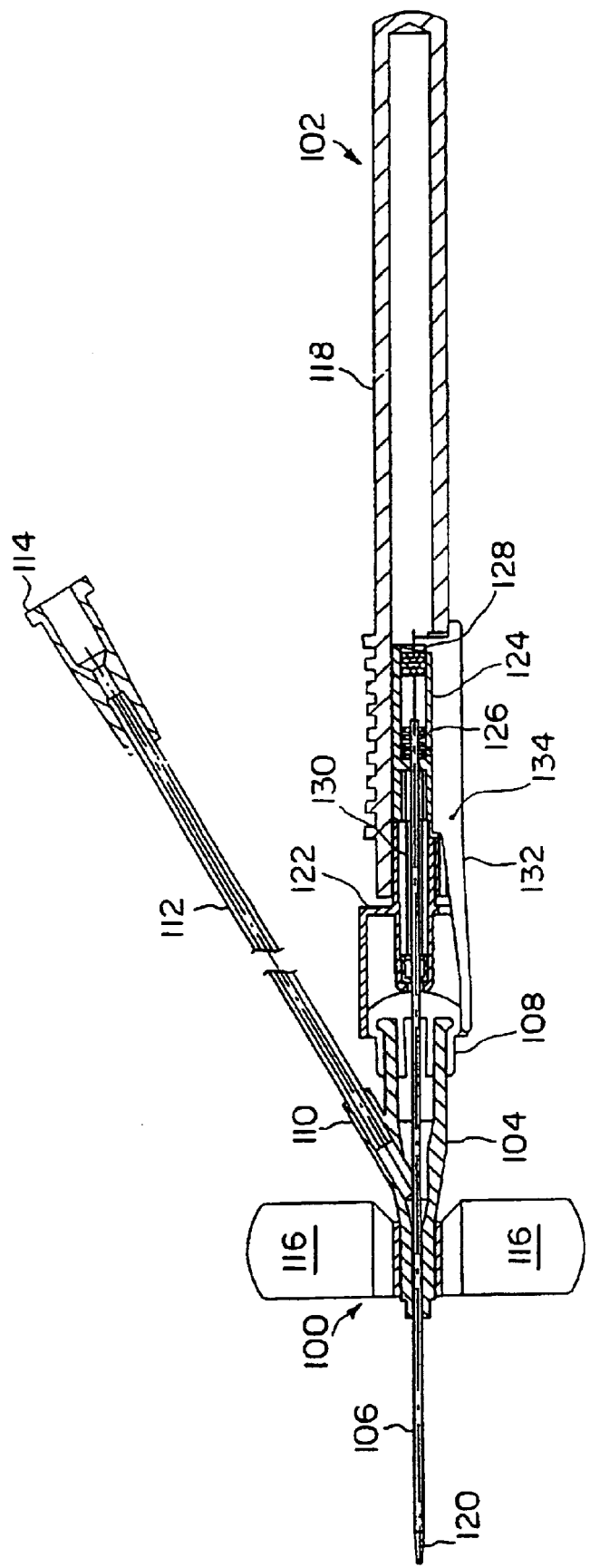
FIG. 4 is a sectional view of a Y-port catheter and an insertion device therefor shown in an initial assembled configuration.

Referring now to FIG. 4, there is shown an Y-port catheter 100, and an insertion device 102 for inserting the catheter 100 into a blood vessel of a patient or into the septum of an in-line intravenous infusion device such as a Y-site. The catheter 100 has a hollow body 104 with a tapered front end for holding a flexible catheter cannula 106 in fluid communication with the interior of the body 104. The rear of the catheter 100 has a piercable septum 108 held thereon or other fluid communication port provided for attachment of further intravenous infusion devices. The piercable septum 108 seals the rear portion of the body 104. In addition, a sharp instrument, such as a needle, may De inserted into the rear of the body. The piercable septum forms a fluid seal about such an instrument when the instrument is inserted through septum 108. A pair of flat, flexible wings 116 may be provided to extend from respective opposite sides of the body 104, in order to provide a means of securing the catheter 100 to a patient's body or other surface with adhesive tape.

A branch conduit 110 is formed on one side of the body 104 of the catheter 100. The interior of the branch conduit 110 is in fluid communication with the interior of the body 104. The branch conduit further connects with a fluid supply or withdrawal line 112 so that two fluid paths are provided through the catheter 106. One fluid path extends from the catheter cannula 106 to the septum 108. The other fluid path leads from the catheter cannula 106 through the branch conduit 100. Further intravenous devices may be connected to the branch conduit 110, such as the fluid line 112, which is shown in FIG. 4 to connect with a luer hub 114.

The insertion device 102 has a generally tubular barrel 118 from which a needle 120 extends from the front end thereof in an initial configuration of the insertion device 102. In the initial configuration, the needle is positioned to extend through the septum 108 of the catheter, and further through the body 104 of the catheter 100. The needle 120 further extends through the catheter cannula 106, which is supported upon the needle 120 before and during insertion of the catheter cannula 106 into a patient or into a port of a further intravenous infusion device.

A nose piece 122 is positioned at the forward end of the barrel 118. The nose piece 122 has a tubular rear portion which is rigidly held within the barrel 118. The forward end of the nose piece 122 forms a housing shaped to hold the rear end of the catheter 100 therein. Specifically, the housing on the forward end of the nose piece 122 surrounds the outer periphery of the septum 108 so that the catheter 100 is removably held in the forward portion of the insertion device 102. The front end of the nose piece 122 has an aperture formed therein to allow the needle 120 to pass through the hollow interior of the nose piece 122.

The rear end of the needle is secured to a flash chamber 124 positioned within the barrel 118. The flash chamber 124 has an opening at the forward end thereof to allow the rear end of the needle 120 to enter the flash chamber 124, wherein the needle may be secured by adhesive 126. Hence, the flash chamber 124 provides a needle holding assembly for holding the needle 120 in alignment with the barrel 118. A hydrophobic vent 128 is positioned in the rear portion of the flash chamber to allow gas to be vented from the interior of the flash chamber when fluid, such as blood, is passed through the needle upon insertion of the catheter into a patient.

The flash chamber 124 is slidably positioned within the barrel 118, and is biased toward the rear of the barrel 118 by a spring 130. The spring 130 is compressed between the forward end of the flash chamber 124 and the forward interior surface of the nose piece 122. In the initial configuration, movement of the flash chamber 124 is restrained by a lever 132. The central portion of the lever 132 extends in parallel along the barrel 118, and is held to the barrel 118 by a pivot 134. The rear portion of the lever 132 is formed to extend along the barrel and has an abutment extending into the barrel 132. The abutment at the rear portion of the lever has a forward abutment surface in slidable engagement with the rear of the flash chamber 124. As can been seen in FIG. 4, the rear of the flash chamber and the forward abutment surface of the rear portion of the lever 132 are mutually canted to provide a camming bias urging the rear portion of the lever out of the barrel, and out of engagement with the flash chamber. The forward portion of the lever 132 extends in parallel with the barrel 118. An inward surface of the forward portion of the lever 132 abuts against the catheter 100, and specifically against the the outer rim of the septum 108. Thus the camming bias against the rear portion of the lever is restrained by the abutment between the forward end of the lever and the catheter 100.

In order to insert the catheter 100 into an injection site in a patient or other intravenous fluid injection site, the barrel is held between one finger positioned on a grip area 134 on one side of the barrel 118 and another finger positioned on the rear portion of the lever along the other side of the barrel 118. The needle 120 may then be inserted into the injection site in order to guide the catheter cannula into the site. When the cannula is suitably positioned at the injection site, the catheter 100 is held in place while the insertion device 102 is moved rearwardly to disengage the insertion device 102 from the catheter 100 and to withdraw the needle from the catheter 100 through the septum 108. As the insertion device 102 is uncoupled from the catheter 100, the operator may maintain pressure upon the rear portion of the lever 132, or may remove pressure from the lever 132 to allow retraction of the needle as soon as the tip of the needle is withdrawn from the septum 108.

Referring now to FIG. 5, the catheter insertion device 102 and the catheter 100 are illustrated in a configuration in which the operator has withdrawn the needle nearly completely from the catheter 100, and has released the lever 132. Upon release of the lever after withdrawal of the catheter 100, the forward portion of the lever is no longer restrained by abutment with the catheter 100. Thus the camming bias between the flash chamber and the rear end of the lever urges the rear portion of the lever to move away from the barrel 118 so that the rear abutment surface lever is urged out the barrel. Prior to the tip of the needle being withdrawn from the septum 108, the flash chamber 124 will remain substantially in the forward portion of the barrel due to friction between the needle 122 and the septum 108. Upon removal of the needle from the septum 108 and disengagement of the camming abutment between the lever 132 and the flash chamber 124, the spring 130 then pushes the flash chamber 124 into the rear interior portion of the barrel 118 so that the needle is safely retracted into the barrel as shown in the configuration of FIG. 6. Retraction of the needle may alternatively be delayed by the operator by maintaining pressure upon the rear portion of the lever 132 until retraction is desired.

The terms and expressions which have been employed are used as terms of description and not of limitation. There is no intention in the use of such terms and expressions of excluding any equivalents of the features shown and described or portions thereof. It is recognized, however, that various modifications are possible within the scope and spirit of the invention. Accordingly, the invention incorporates variations that fall within the scope of the following claims.

What is claimed is:

1. A medical device configured for connection with an infusion device, comprising:
   a housing;
   a needle projecting forwardly from the housing;
   a biasing element biasing the needle rearwardly;
   a needle retainer releasably retaining the needle against the bias of the biasing element;
   a Y-port slidably displaceable within the housing, comprising:
      a first conduit in fluid communications with the needle; and
      a second conduit transverse the first conduit, in fluid communication with the needle;
   an actuator operable to release the needle from the needle retainer; and
   a connector projecting forwardly from the housing and circumscribing the needle, for coupling with the infusion device.

2. The device of claim 1 wherein the actuator is manually actuable.

3. The device of claim 1 wherein the first conduit has a generally open end and the device comprises a piercable seal sealing the open end of the first conduit.

4. The device of claim 1 wherein the device comprises a rearward stop limiting the rearward displacement of the needle after retraction.

5. The device of claim 1 wherein the device comprises a forward stop limiting the forward displacement of the needle after retraction.

6. A medical device comprising:
   a longitudinally elongated hollow housing having a generally open rearward end;
   a Y-port slidably displaceable within the housing, comprising:

a first conduit substantially axially aligned with the longitudinal axis of the housing;

a second conduit transverse the first conduit;

a needle fixedly connected to the Y-port, projecting forwardly from the housing, wherein the needle is in fluid communication with the first and second conduits of the Y-port;

a biasing element biasing the Y-port rearwardly;

a manually actuable actuator operable to release the Y-port so that the biasing element propels the Y-port rearwardly.

7. The device of claim 6 wherein the first conduit has a generally open end and the device comprises a piercable seal sealing the open end of the first conduit.

8. The device of claim 6 wherein the device comprises a rearward stop limiting the rearward displacement of the needle after retraction.

9. The device of claim 6 wherein the device comprises a forward stop limiting the forward displacement of the needle after retraction.

10. An apparatus comprising:

a catheter having a forward cannula portion and a body portion; and an insertion device disengageably connected with the catheter, the insertion device having:

a barrel;

a forward engagement portion connected with the barrel for holding the catheter in engagement with the barrel in an initial configuration;

a needle holding assembly slidably positioned within the barrel;

a needle connected to the needle holding assembly and extending from the front of the barrel in the initial configuration;

a spring positioned between the forward engagement portion and the needle holding assembly for exerting a rearward bias upon the needle holding assembly in the initial configuration;

a lever pivotable between a locked position and an unlocked position, having a forward portion abutting the catheter at the forward engagement portion of the barrel in the initial configuration, preventing the lever from being displaced into the unlocked Position, wherein in the locked position the lever retains the needle in the extended position against the bias of the biasing element and in the unlocked position the biasing element is operable to displace the needle into the retracted position;

wherein upon removal of the catheter from the device, the catheter disengages the lever, allowing the lever to be displaced into the unlocked position.

11. The apparatus of claim 10 wherein the body portion of the catheter is formed to provide a first fluid path extending from the cannula to a rear end of the body portion and a second fluid path extending from the cannula to a branch conduit formed in the body portion.

12. The apparatus of claim 11 wherein a piercable septum is positioned on the rear of the body portion, and wherein the needle extends through the piercable septum in the initial configuration.

13. The apparatus of claim 10 wherein the lever is positioned along one side of the barrel allowing selective release of the lever when the needle has been withdrawn from the catheter.

14. The apparatus of claim 10 wherein the needle holding assembly is configured to provide a flash back chamber.

15. The insertion device of claim 10 wherein the catheter comprises a pierceable septum and the needle extends through the septum with sufficient friction therebetween during disengagement of the insertion device from the catheter to prevent motion of the needle holding assembly due to the rearward bias.

16. The insertion device of claim 10 wherein the catheter comprises a pierceable septum that the needle projects through in the initial position, wherein the frictional force between the needle and the septum is greater than the biasing force of the biasing element, such that the septum retains the needle against retraction after the lever pivots into the unlocked position.

* * * * *

UNITED STATES PATENT AND TRADEMARK OFFICE
CERTIFICATE OF CORRECTION

PATENT NO. : 6,921,391 B1
DATED : August 9, 2005
INVENTOR(S) : John Barker et al.

It is certified that error appears in the above-identified patent and that said Letters Patent is hereby corrected as shown below:

<u>Title page,</u>
Item [63], Related U.S. Application Data, replace paragraph with the paragraph below;
-- Provisional Application No. 60/098,280, filed Aug. 28, 1998. --.

Signed and Sealed this

Eleventh Day of October, 2005

JON W. DUDAS
*Director of the United States Patent and Trademark Office*